(12) United States Patent
Viola (10) Patent No.: US 7,434,716 B2
(45) Date of Patent: Oct. 14, 2008

(54) STAPLE DRIVER FOR ARTICULATING SURGICAL STAPLER

(75) Inventor: Frank J. Viola, Sandy Hook, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

(21) Appl. No.: 11/643,074

(22) Filed: Dec. 21, 2006

(65) Prior Publication Data

US 2008/0149684 A1    Jun. 26, 2008

(51) Int. Cl.
*A61B 17/068* (2006.01)

(52) U.S. Cl. .................. 227/176.1; 227/19; 606/206; 606/219

(58) Field of Classification Search .......... 227/19, 227/175.1, 176.1, 180.1; 606/16, 205, 52, 606/144, 207, 208, 139, 219; 604/22

See application file for complete search history.

(56) References Cited

U.S. PATENT DOCUMENTS

| | | | |
|---|---|---|---|
| 3,079,606 A | 3/1963 | Bobrov et al. | |
| 3,252,643 A | 5/1966 | Strekopytov et al. | |
| 3,317,105 A | 5/1967 | Astafjev et al. | |
| 3,490,675 A | 1/1970 | Green et al. | |
| 3,499,591 A | 3/1970 | Green | |
| 4,111,206 A | 9/1978 | Vishnevsky et al. | |
| 4,244,372 A | 1/1981 | Kapitanov et al. | |
| 4,605,001 A | 8/1986 | Rothfuss et al. | |
| 4,610,383 A * | 9/1986 | Rothfuss et al. ............... | 227/19 |
| 4,633,874 A | 1/1987 | Chow et al. | |
| 4,767,044 A | 8/1988 | Green | |
| 4,880,015 A * | 11/1989 | Nierman ...................... | 600/564 |
| 4,978,049 A | 12/1990 | Green | |
| 5,014,899 A | 5/1991 | Presty et al. | |
| 5,040,715 A | 8/1991 | Green et al. | |
| 5,156,315 A | 10/1992 | Green et al. | |
| 5,209,747 A * | 5/1993 | Knoepfler ..................... | 606/16 |
| 5,217,472 A | 6/1993 | Green et al. | |
| 5,253,793 A | 10/1993 | Green et al. | |
| 5,257,713 A | 11/1993 | Green et al. | |
| 5,289,963 A | 3/1994 | McGarry et al. | |
| 5,312,023 A | 5/1994 | Green et al. | |
| 5,318,221 A | 6/1994 | Green et al. | |
| 5,356,064 A | 10/1994 | Green et al. | |
| 5,364,001 A | 11/1994 | Bryan | |
| 5,364,002 A | 11/1994 | Green et al. | |
| 5,364,003 A | 11/1994 | Williamson, IV | |
| 5,392,978 A | 2/1995 | Velez et al. | |
| 5,397,046 A | 3/1995 | Savage et al. | |
| 5,405,344 A * | 4/1995 | Williamson et al. ............ | 606/1 |
| 5,413,268 A | 5/1995 | Green et al. | |
| 5,413,272 A | 5/1995 | Green et al. | |
| 5,415,334 A | 5/1995 | Williamson, IV et al. | |

(Continued)

*Primary Examiner*—Scott A. Smith (57) ABSTRACT

An articulating surgical instrument is provided including a handle, an articulating portion extending distally of the handle and an end effector positioned on a distal end of the articulating portion. A flexible drive band is provided for movement through the articulating portion and end effector. The flexible drive band includes a first portion having a first height and the second portion having a second height greater than the first height. The difference in heights being sufficient to eject staples from a body portion of the end effector into an anvil member of the end effector. An actuation mechanism is provided for drawing the flexible drive band through the articulating surgical instrument.

15 Claims, 5 Drawing Sheets

U.S. PATENT DOCUMENTS

| | | |
|---|---|---|
| 5,417,361 A | 5/1995 | Williamson, IV |
| 5,425,745 A | 6/1995 | Green et al. |
| 5,431,322 A | 7/1995 | Green et al. |
| 5,439,155 A | 8/1995 | Viola |
| 5,465,895 A | 11/1995 | Knodel et al. |
| 5,472,132 A | 12/1995 | Savage et al. |
| 5,476,206 A | 12/1995 | Green et al. |
| 5,478,003 A | 12/1995 | Green et al. |
| 5,482,197 A * | 1/1996 | Green et al. ............ 227/178.1 |
| 5,485,952 A | 1/1996 | Fontayne |
| 5,487,499 A | 1/1996 | Sorrentino et al. |
| 5,489,058 A | 2/1996 | Plyley et al. |
| 5,497,933 A | 3/1996 | DeFonzo et al. |
| 5,509,596 A | 4/1996 | Green et al. |
| 5,517,997 A | 5/1996 | Fontenot |
| 5,535,935 A | 7/1996 | Vidal et al. |
| 5,540,375 A | 7/1996 | Bolanos et al. |
| 5,549,637 A * | 8/1996 | Crainich ................ 606/207 |
| 5,554,169 A | 9/1996 | Green et al. |
| 5,558,266 A | 9/1996 | Green et al. |
| 5,562,241 A | 10/1996 | Knodel et al. |
| 5,564,615 A | 10/1996 | Bishop et al. |
| 5,577,654 A | 11/1996 | Bishop |
| 5,579,978 A | 12/1996 | Green et al. |
| 5,584,425 A | 12/1996 | Savage et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,615,820 A | 4/1997 | Viola |
| 5,626,587 A | 5/1997 | Bishop et al. |
| 5,630,540 A | 5/1997 | Blewett |
| 5,630,541 A | 5/1997 | Williamson, IV et al. |
| 5,634,584 A | 6/1997 | Okorocha et al. |
| 5,645,209 A | 7/1997 | Green et al. |
| 5,647,526 A | 7/1997 | Green et al. |
| 5,662,258 A | 9/1997 | Knodel et al. |
| 5,662,662 A | 9/1997 | Bishop et al. |
| 5,690,269 A | 11/1997 | Bolanos et al. |
| 5,706,997 A | 1/1998 | Green et al. |
| 5,709,334 A | 1/1998 | Sorrentino et al. |
| 5,711,472 A * | 1/1998 | Bryan .................... 227/175.1 |
| 5,738,474 A | 4/1998 | Blewett |
| 5,749,893 A | 5/1998 | Vidal et al. |
| 5,762,255 A | 6/1998 | Chrisman et al. |
| 5,797,537 A | 8/1998 | Oberlin et al. |
| 5,816,471 A | 10/1998 | Plyley et al. |
| 5,817,109 A | 10/1998 | McGarry et al. |
| 5,820,009 A | 10/1998 | Melling et al. |
| 5,826,776 A * | 10/1998 | Schulze et al. ............ 227/176.1 |
| 5,865,361 A | 2/1999 | Milliman et al. |
| 5,871,135 A | 2/1999 | Williamson, IV et al. |
| 5,878,937 A | 3/1999 | Green et al. |
| 5,918,791 A | 7/1999 | Sorrentino et al. |
| 5,941,442 A | 8/1999 | Geiste et al. |
| 6,010,054 A | 1/2000 | Johnson et al. |
| 6,079,606 A | 6/2000 | Milliman et al. |
| 6,109,500 A | 8/2000 | Alli et al. |
| 6,202,914 B1 | 3/2001 | Geiste et al. |
| 6,241,139 B1 | 6/2001 | Milliman et al. |
| 6,241,140 B1 * | 6/2001 | Adams et al. ............ 227/180.1 |
| 6,330,965 B1 | 12/2001 | Milliman et al. |
| 6,533,157 B1 * | 3/2003 | Whitman ................ 227/175.1 |
| 6,619,529 B2 | 9/2003 | Green et al. |
| 6,644,532 B2 | 11/2003 | Green et al. |
| 6,663,641 B1 * | 12/2003 | Kovac et al. ............... 606/144 |
| 6,669,073 B2 | 12/2003 | Milliman et al. |
| 6,681,978 B2 | 1/2004 | Geiste et al. |
| 6,716,232 B1 | 4/2004 | Vidal et al. |
| 6,742,692 B2 * | 6/2004 | Hartwick ................ 227/176.1 |
| 6,793,652 B1 | 9/2004 | Whitman et al. |
| 6,817,509 B2 * | 11/2004 | Geiste et al. ............ 227/176.1 |
| 6,830,174 B2 * | 12/2004 | Hillstead et al. ......... 227/175.1 |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,877,647 B2 | 4/2005 | Green et al. |
| 6,913,613 B2 * | 7/2005 | Schwarz et al. ............ 606/206 |
| 6,953,139 B2 | 10/2005 | Milliman et al. |
| 6,981,941 B2 | 1/2006 | Whitman et al. |
| 7,032,798 B2 | 4/2006 | Whitman et al. |
| 7,044,353 B2 | 5/2006 | Matri et al. |
| 7,055,730 B2 | 6/2006 | Ehrenfels et al. |
| 7,077,856 B2 | 7/2006 | Whitman |
| 7,087,071 B2 | 8/2006 | Nicholas et al. |
| 7,097,089 B2 | 8/2006 | Marczyk |
| 7,114,642 B2 | 10/2006 | Whitman |
| 7,128,253 B2 | 10/2006 | Mastri et al. |
| 7,143,924 B2 | 12/2006 | Scirica et al. |
| 7,235,089 B1 * | 6/2007 | McGuckin, Jr. ............ 606/167 |
| 2004/0232200 A1 | 11/2004 | Shelton, IV et al. |
| 2006/0016853 A1 | 1/2006 | Racenet |
| 2007/0262116 A1 | 11/2007 | Hueil et al. |

* cited by examiner

STAPLE DRIVER FOR ARTICULATING SURGICAL STAPLER

BACKGROUND

1. Technical Field

The present disclosure relates to a staple driver for an articulating surgical stapling instrument. More particularly, the present disclosure relates to a staple driver for use in a surgical stapling instrument capable of articulating greater than 90 degrees.

2. Background of Related Art

Various types of surgical staplers are known for stapling tissue within the body. Some such surgical staplers are configured to bend or articulate at a point along a distal shaft or adjacent to an end effector associated with the stapler. These surgical staplers generally include a staple containing distal end configured to eject staples into tissue. A driving member is associated with the surgical stapler and is driven distally upon actuation to eject the staples into tissue.

Occasionally, as the driving member is moved distally through the surgical stapler, the driving member may have a tendency to bow or buckle outwardly at the bend or articulation point along the surgical stapler. This can reduce the effectiveness of the surgical staple or, in some cases, incapacitate the stapler entirely.

Thus, it is desirable to provide an articulating surgical stapler having a staple driving assembly configured to prevent bowing or buckling of the driving member as the stapler is actuated to drive staples into tissue.

SUMMARY

The presently disclosed staple driving assembly generally includes a cartridge having a body portion defining at least one staple containing pocket and an elongated band movably mounted within the body portion. The band is movable beneath the at least one staple containing pocket such that the band urges a staple contained within the pocket into tissue. The elongated band is formed as a flexible member movable within the body portion. The elongated band generally includes a first portion having a first height and a second portion having a second height greater than the first height. The difference between the first and second heights being sufficient to eject a staple from within the staple containing pocket.

In one embodiment, the band can include a third portion having a height less than the second portion. In an alternative embodiment, the band can include a third portion having a height substantially equal to that of the second portion.

In a particular embodiment, the body portion may include a first staple containing pocket on a first side of the body portion and a second staple containing pocket on the second side of the body portion. A post is positioned intermediate the first and second sides such that the elongated band can pass around the post and beneath the first and second staple containing pockets. The post may be configured as a roller positioned at a distal end of the body portion. The body portion may include a pusher positioned between a staple contained within the staple containing pocket and the elongated band to receive pressure from the elongated band and transfer it to the staple.

There is also disclosed a surgical instrument having a handle, an articulating elongate tubular member extending distally from the handle and a staple clinching assembly provided at a distal end of the elongate tubular member. The staple clinching assembly includes a staple driving assembly and an anvil member movable relative to the staple driving assembly. The staple driving assembly includes a plurality of staple containing pockets. Staples are positioned within the staple containing pockets and pushers are positioned between the staples and an elongated driving band which is movably mounted within surgical instrument.

The surgical instrument includes an actuation mechanism which is configured to draw the elongated driving band distally such that the elongated driving band can pass around an articulating section of the surgical instrument without risk of bowing or flexing.

The surgical instrument additionally includes a camming mechanism configured to cam an anvil member of the surgical instrument relative to the staple driving assembly.

DESCRIPTION OF THE DRAWINGS

Various embodiments of the presently disclosed staple driver for use in an articulating surgical stapling device are disclosed herein with reference to the drawings, wherein.

DETAILED DESCRIPTION OF EMBODIMENTS

Embodiments of the presently disclosed staple driving assembly for use with an articulating surgical stapler will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
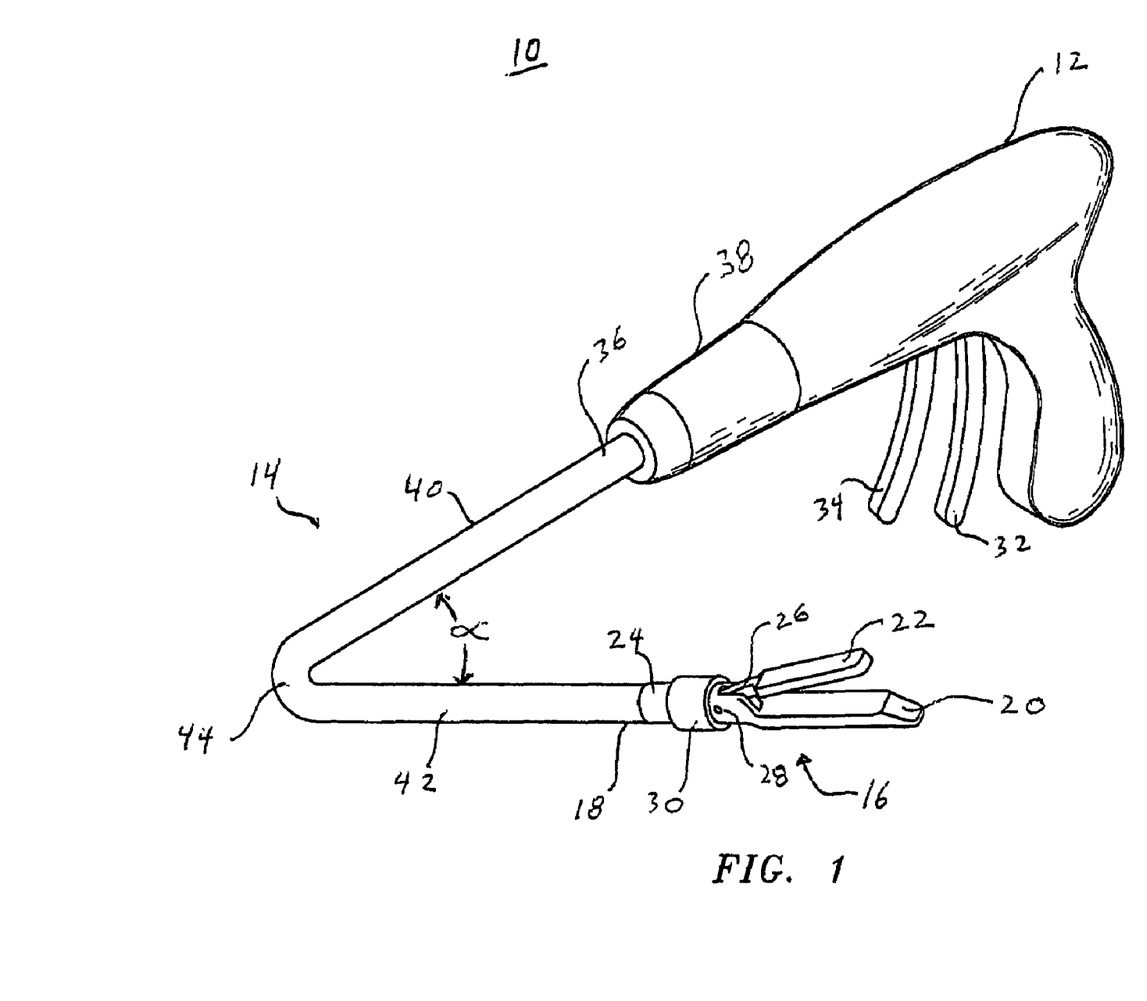
FIG. 1 is a perspective view of an articulating surgical stapler.

FIG. 1 illustrates one embodiment of an articulating surgical stapler 10. Surgical stapler 10 generally includes a handle 12 and an elongated tubular member 14 extending distally from handle 12. A staple clinching assembly 16 is provided on a distal end 18 of elongated tubular member 14. Staple clinching assembly 16 includes a staple driving assembly 20 and an anvil member 22 pivotally affixed to a proximal end 24 of staple driving assembly 20. Anvil member 22 is movable from an open position spaced apart from staple driving assembly 20 to a closed position generally adjacent staple driving assembly 20. Specifically, a proximal end 26 of anvil member 22 is pivotally affixed to staple driving assembly 20 at a pivot point 28.

In order to move anvil member 22 between the open and closed positions, staple clinching assembly 16 additionally includes a sliding or camming collar 30 which is provided to engage and move anvil member 22 in a manner described in more detail hereinbelow. A first trigger 32 is provided on handle 12 to move collar 30 distally and proximally relative to elongated tubular member 14 in order to open and close anvil member 22. A second trigger 34 is provided on handle 12 to actuate staple driving assembly 20 and drive staples (FIG. 2) out of staple driving assembly 20 and into anvil member 22.

As noted hereinabove, various types of articulating surgical staplers are known in the art. Surgical stapler 10 is configured to articulate at a point along elongated tubular member 14. Specifically, elongated tubular member 14 includes a proximal end 36 which extends distally from a nose cone portion 38 of handle 12. Elongated tubular member 14 includes a proximal section 40 and a distal section 42. Elongated tubular member 14 is configured to articulate at an intermediate portion 44 located between proximal and distal sections 40 and 42, respectively. In this particular embodiment, intermediate portion 44 has the ability to bend through an angle α which is greater than 90 degrees and may be up to almost 180 degrees.

Referring now to FIGS. 2-5, the details of staple clinching assembly 16 will now be described. Initially with regard to FIGS. 2 and 3, as noted hereinabove, and anvil member 22 is movable between an open position spaced from staple driving assembly 20 to a closed positions substantially adjacent to staple driving assembly 20. Camming collar 30 includes a leading edge 46 which is configured to engaged a sloped surface 48 formed on proximal end 26 of anvil member 22. In order to move camming collar 30, there is provided a continuous loop cable 50 which extends from handle 12 through elongate tubular number 14 and through staple driving assembly 20.

Figure 3:
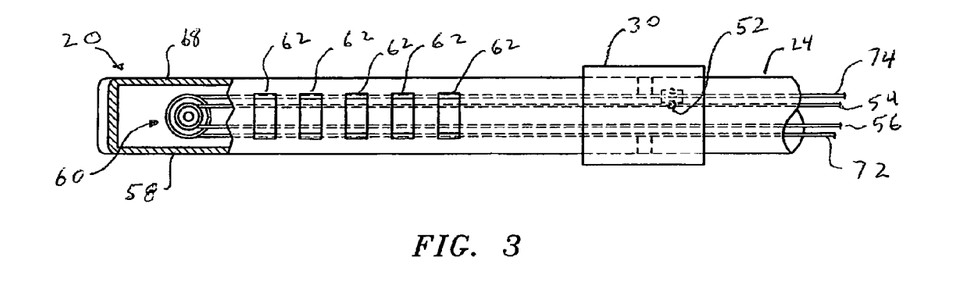
FIG. 3 is a top view, partially shown in section, of the distal end of the surgical stapler.

Referring for the moment specifically to FIG. 3, cable 50 is affixed to one side of camming collar 30 at a fixation point 52. In this particular embodiment, fixation point 52 is attached to an advancing side 54 of cable 50 while a retracting side 56 is free to slide through camming collar 30. A body portion 58 of staple driving assembly 20 is provided with a compound roller 60 to accommodate the passage and movement of cable 50 through staple driving assembly 20. Cable 50 passes around a portion of compound roller 60 in a manner described in more detail hereinbelow. By moving advancing side 54 distally relative to staple driving assembly 20, advancing side 54 of cable 50 moves camming collar 30 distally causing leading edge 46 to engage sloped surface 48 of anvil member 22 and move anvil member 22 to a closed position relative to staple driving assembly 20. It should be noted that since cable 50 forms a continuous loop within articulating surgical instrument 10 around compound roller 60, constant tension is applied to both advancing side 54 and retracting side 56 of cable 50 thereby preventing any buckling or bowing of cable 50 as it passes through intermediate articulating section 44 of elongate tubular member 14.

Referring again to FIGS. 2 and 3, staple clinching assembly 16 is provided to advance a row of staples out of staple driving assembly 20 and into anvil member 22 in order to staple tissue captured therebetween. Thus, body portion 58 of staple driving assembly 20 contains a plurality of staple containing pockets 62 formed therein. Staples 64 are provided within staple containing pockets 62 and pushers 66 are positioned within staple containing pockets 62 below staples 64. By advancing pushers 66 upwardly within staple containing pockets 62, staples 64 are advance out of staple containing pockets 62 and into anvil member 22. As noted hereinabove, compound roller 60 is provided at a distal end 68 of body portion 58 to provide a return path for cable 50 as well as aid in maintaining constant pressure on cable 50 as it passes through stapler 10.

Figure 2:
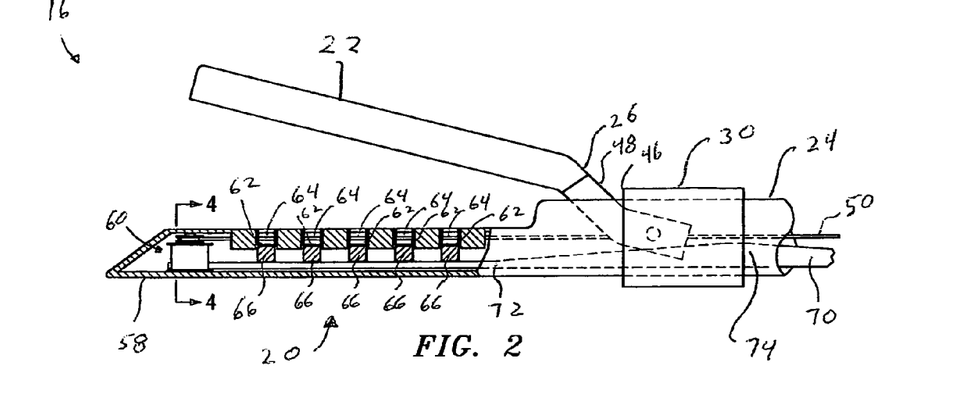
FIG. 2 is a side view, partially shown in section, of the distal end of the surgical stapler.

In order to advance pushers 66 upwardly, and thus drive staples 64 out of staple containing pockets 62, staple driving assembly 20 is provided with a novel driver or flexible drive band 70 which extends from handle 12 through elongate tubular member 14 and into staple driving assembly 20. Drive band 70 passes around compound roller 60 and back through a return path to handle 12. Drive band 70 is positioned within body portion 58 such that drive band 70 passes directly beneath staple containing pockets 62. Similar to cable 50, drive band 70 is maintained under constant tension so as to prevent any buckling or bowing of drive band 70 as it passes through intermediate articulating section 44 of elongate tubular member 14. In order to move pushers 66 within staple containing pockets 62, drive band 70 includes a first or leading portion 72 and a second or driving portion 74 having a height greater than leading portion 72. Thus, as driving portion 74 passes beneath staple containing pockets 62, driving portion 74 forces pushers 66 and staples 64 upwardly within staple containing pockets 62.

Figure 4:
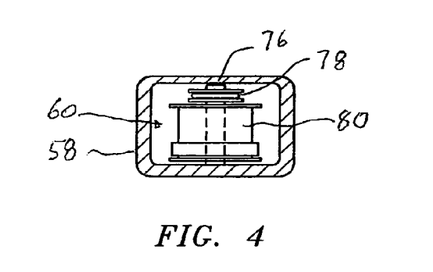
FIG. 4 is an end view, partially shown in section, taken along the line 4-4 of FIG. 2.
Figure 5:
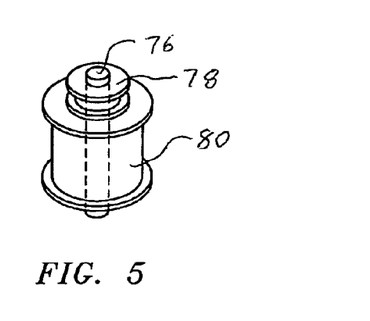
FIG. 5 is a perspective view of a dual roller mechanism.

Referring for the moment to FIGS. 4 and 5, and as noted hereinabove, body portion 58 of staple driving assembly 20 is provided with a compound roller 60. Compound roller 60 provides a return path for cable 54 as well as flexible drive band 70. Compound roller 60 additionally assists in providing constant tension on cable 54 and flexible drive band 70 to prevent cable 54 and flexible drive band 70 from flexing or bowing as they pass through articulating section 44 of elongate tubular member 14. Specifically, compound roller 60 is affixed within distal end 68 of body portion 58 by a pin 76. In one particular embodiment, compound roller 60 includes a cable roller 78 and a band roller 80. Cable roller 78 and band roller 80 are free to rotate independently about pin 76 to accommodate the independent motions of cable 54 and flexible drive band 70.

Figure 6:
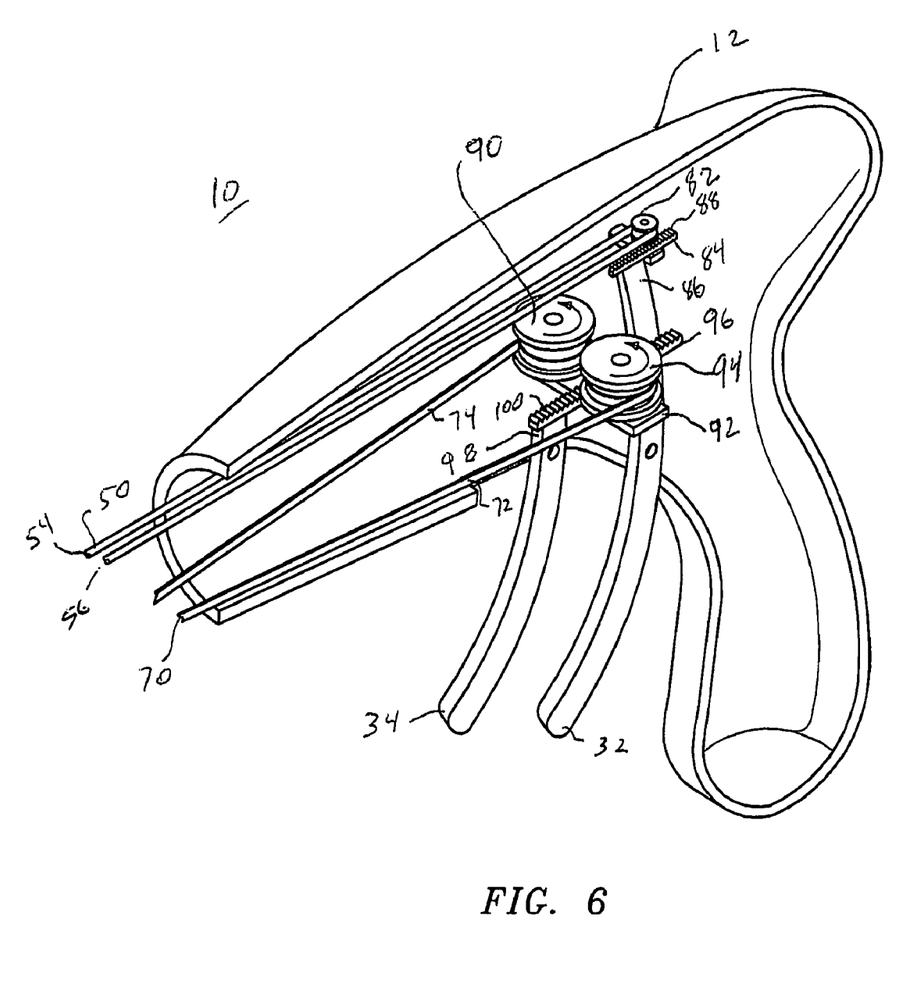
FIG. 6 is a perspective view of the handle mechanism of FIG. 1 with half of the handle housing removed.

Referring now to FIG. 6, the use of first trigger 32 and second trigger 34 on handle 12 to actuate cable 50 and flexible drive band 70, respectively, will now be described. A cable drive wheel 82 is rotatably mounted within handle 12. Cable drive wheel 82 provides a second end for tensioning the continuous loop of cable 50 as well as a means of advancing and retracting cable 50 through surgical instrument 10. Specifically, a rack 84 provided on an upper portion 86 of first trigger 32 includes a plurality of teeth 88 which are configured to engage corresponding teeth (not shown) on an underside of drive wheel 82 to thereby rotate drive wheel 82 in response to actuation of first trigger 32. As first trigger 32 is actuated, drive wheel 82 is rotated so as to pull on retracting side 56 of cable 50. As retracting side 56 is pulled proximally, advancing side 54 of cable 50 moves distally so as to cause camming collar 32 moves distally and force anvil member 22 to a closed position. Likewise, as first trigger 32 is released, drive wheel 82 rotates in an opposite direction so as to draw collar 32 proximally and allow anvil member 22 to move to the open position.

As noted hereinabove, articulating surgical stapler 10 incorporates novel flexible drive band 70 to eject staples 64 out of staple driving assembly 20. Unlike conventional articulating surgical staplers, which push or force flexible driving members about an articulation point along the surgical stapler, flexible drive band 70 is tensioned or drawn distally through the articulation point during actuation thereby eliminating any possibility that flexible drive band 70 will bow or flex outwardly at the point of articulation.

Staple driving assembly 20 includes a first or payout spool 90 about which a portion of flexible drive band 70 is positioned. Payout spool 90 is rotatably affixed to a mounting bar 92 positioned within handle 12. Payout spool 90 can be provided with various spring or friction devices to provide a slight amount of proximal tension on flexible drive band 70. Staple driving assembly 20 additionally includes a second or driving spool 94 also rotatably mounted to mounting bar 92. Driving spool 94 is configured to draw flexible drive band 70 through elongate tubular member 14, around band roller 80 and back through elongate tubular member 14. Specifically, second trigger 34 is provided with a rack 96 on an upper portion 98 of second trigger 34. Rack 96 includes teeth 100 which are configured to engage corresponding teeth on an underside of driving spool 94 in order to rotate driving spool 94 in response to actuation of second trigger 34.

Thus, upon actuation of second trigger 34, drive spool 94 it is rotated so as to draw first or leading portion 72 of flexible drive band 70 proximally causing second or driving portion 74 of flexible drive band 70 to move distally through elongate tubular member 14 and beneath pushers 66 located within staple driving assembly 20. It should be noted that, in order to draw driving portion 74 fully beneath all pushers 66 located within staple driving assembly 20, it may be necessary to actuate second trigger 34 several times. In this event, known adaptations to rack 96 can be provided to allow rack 96 to reset relative to driving spool 94 for further or multiple activations.

Figure 7:
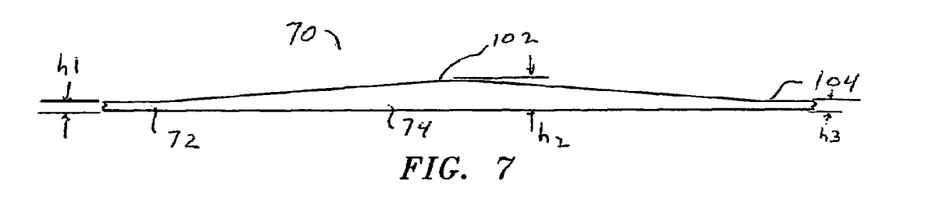
FIG. 7 is a side view of one embodiment of a drive tape for use in the surgical stapler of FIG. 1.

Referring now to FIG. 7, the configuration of one embodiment of flexible drive band 70, including leading portion 72 and driving portion 74 is illustrated. Flexible drive band 70 may be formed from any of various flexible materials including stainless steel, plastics or other polymeric materials which are sufficiently stiff in width so as to drive pushers 66 within staple containing pockets 62.

Leading portion 72 of flexible drive band 70 has a first height h1 which is relatively small to allow easy initial movement of flexible drive band 70 through staple driving assembly 20 and beneath staple pockets 62. Driving portion 74 of flexible drive band 70 has a second height h2 which is greater than that of height h1. Driving portion 74 defines a leading edge 102 at second height h2. The difference in distance between heights h1 and h2 is substantially equivalent to the distance needed to drive pushers 66 within staple containing pockets 62 in order to for staples 64 out of staple pocket 62 and into anvil member 22. It should be noted that band roller 80 has sufficient width to accommodate height h2 of driving portion 74 so that flexible band 70 can be drawn through a first role of staple containing pockets 62, around band roller 80 and back through a second row of staple containing pockets 62 on an opposite side of first row of staple containing pockets 62. In this manner, multiple rows of staple containing pockets 62 may be accommodated within staple driving assembly 20.

Figure 8:
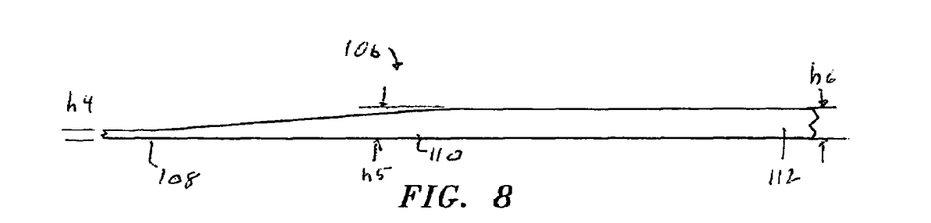
FIG. 8 is a side view of an alternative embodiment of a drive tape.

Referring now to FIG. 8, there is disclosed an alternative embodiment of a flexible drive band 106 for use with staple driving assembly 20. Flexible drive band 106 includes a first or leading portion 108 having a first height h4 and a second or driving portion 110 having a second height h5 sufficient to drive pushers 66 and staples 64 within staple containing pockets 62. A proximal portion 112 of driving portion 110 as a third height h6 which is substantially equal to second height h5. By maintaining the height of proximal portion 112 substantially similar to that of driving portion 110, flexible drive band 106 maintains pushers 66 in an upward condition within staple containing pockets 62, as flexible drive band 106 is drawn their beneath, to maintain pressure on staples 64 against anvil member 22 until all staples 64 have been clinched into anvil member 22.

Figure 9:
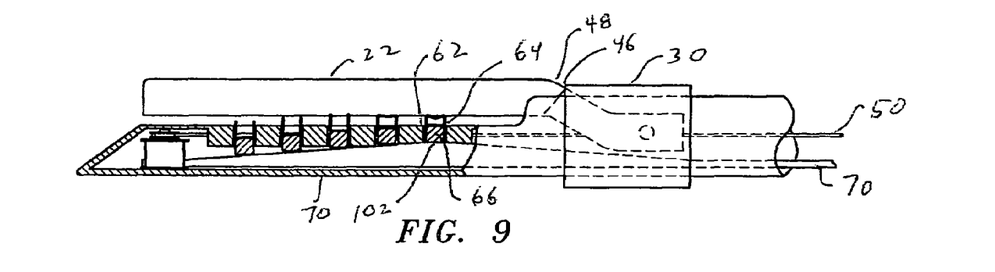
FIG. 9 is a side view, partially shown in section, of the distal end of the surgical stapler during actuation.
Figure 10:
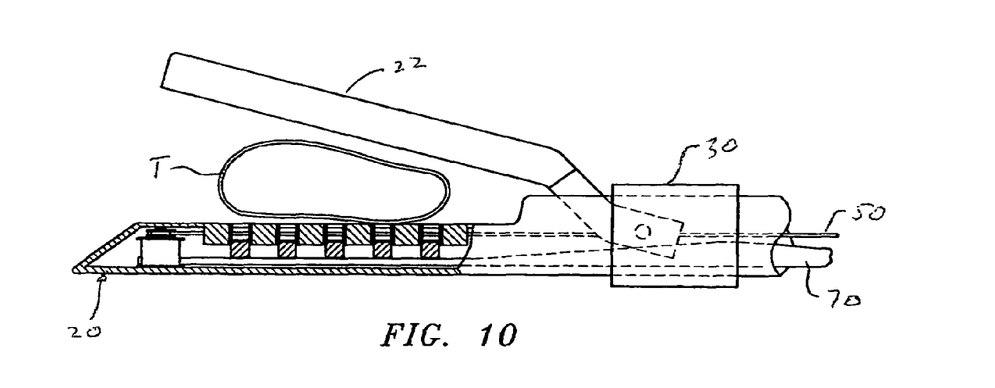
FIG. 10 is a side view, partially shown in section, of the distal end of the surgical stapler position about a tubular tissue section.

As best shown in FIG. 9, camming collar 30 has been moved to a distal most position by cable 50 so as to cause leading edge 46 to urge sloped surface 48 downwardly thereby moving anvil member 22 to a closed position relative to staple driving assembly 20. As further shown in FIG. 9, flexible drive band 70 is illustrated as having moved a distanced distally causing leading edge 102 to urge pushers 66 upwardly within staple containing pockets 62 thereby causing a respective staples 64 to be clinched against anvil member 22.

Referring now to FIGS. 6 and 10 through 13, the use of articulating surgical instrument or stapler 10 to staple tissue will now be described. Initially, with regard to FIG. 10, a tissue T is positioned between anvil member 22 and staple driving assembly 20. Camming collar 30 is in a proximal most position relative to anvil member 22.

Figure 11:
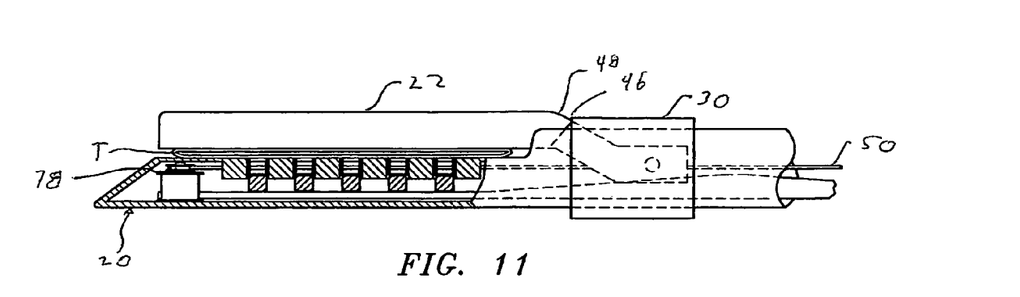
FIG. 11 is a side view, partially shown in section, of the distal end of the surgical stapler with an anvil member cammed against the tissue section.

Referring now to FIGS. 6 and 11, first trigger 32 is initially actuated to move cable 50 through elongate tubular member 14 and about cable roller 78. Specifically, drive wheel 82 is rotated to draw retracting side 56 of cable 50 and to advance advancing side 54 of cable 50. As advancing side 54 of cable 50 moves distally, camming collar 30 moves distally causing leading edge 46 to engage sloped surface 48 on anvil member 22 thereby moving anvil member 22 to a closed position. In this manner, tissue T is captured between anvil member 22 and staple driving assembly 20.

Figure 12:
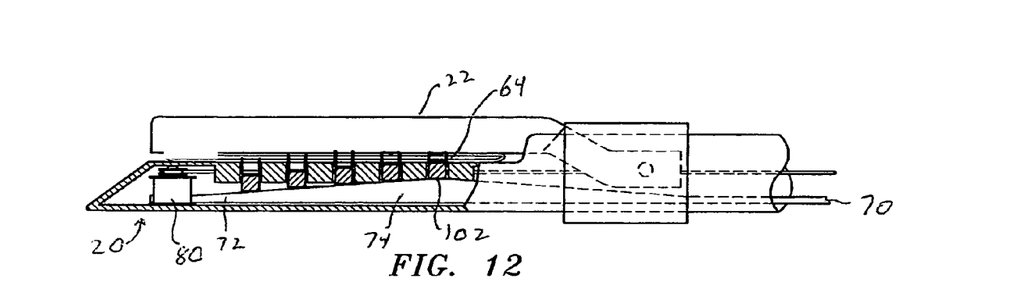
FIG. 12 is a side view, partially shown in section, during actuation of the drive tape to drive staples into the anvil member.
Figure 13:
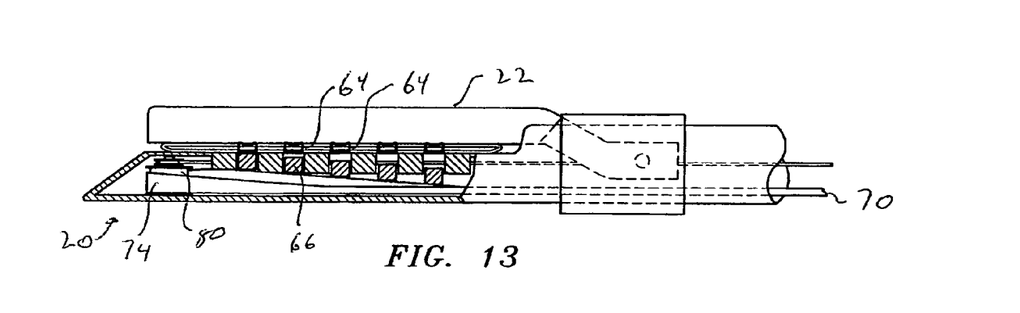
FIG. 13 is a side view, partially shown in section, after complete actuation of the drive tape driving all the staples through the tissue and into the anvil member.

Upon actuation of second trigger 34 (FIG. 6) driving spool 94 it is rotated so as to draw leading portion 72 of flexible drive band 70 proximally while at the same time drawing driving portion 74 distally such that driving portion 74, and thus leading edge 102, passes beneath pushers 66 forcing staples 64 upwardly through tissue T and into anvil member 22 thereby clinching staples 64 through tissue T (FIG. 12). As noted hereinabove, band roller 80 has sufficient width to accommodate driving portion 74 such that driving portion 74 can be drawn proximally beneath a second row of staple containing pockets 62 to clinched a second row of staples 64 into anvil member 22 (FIG. 13).

As discussed hereinabove, provision of flexible drive band 70 along with compound roller 60, allows flexible drive band 70 to be drawn distally through elongate tubular member 14 and about intermediate articulating section 44 (FIG. 1) while at the same time preventing flexible drive band 70 from flexing or bowing outwardly as it passes around intermediate articulating section 44.

It will be understood that various modifications may be made to the embodiments disclosed herein. For example, as noted hereinabove, staple clinching assembly can include multiple rows of staple containing pockets to provide multiple rows of staples through tissue. Further, the disclosed driving member may comprise structure other than a band, such as, for example, a tapered cable etc. which can be drawn distally through an articulating portion of a surgical stapler without fear of buckling or bowing. Therefore, the above description should not be construed as limiting, but merely as exemplifications of particular embodiments. Those skilled in the art will envision other modifications within the scope and spirit of the claims appended hereto.

The invention claimed is:

1. A staple driving assembly comprising:
a cartridge having a body portion, the body portion having a first staple containing pocket and a second staple containing pocket;
an elongated band movably mounted within the body portion. the band being movable beneath the first and second staple containing pockets. such that the elongated band urges a first staple contained within the first staple containing pocket out of the body portion as the elongated band passes beneath the first staple containing pocket in the distal direction and urges a second staple contained within the second staple containing pocket out of the body portion as the elongated band passes beneath the second staple containing pocket in a proximal direction.

2. The staple driving assembly as recited in claim 1, wherein the elongated band is flexible.

3. The staple driving assembly as recited in claim 2, wherein the elongated band has a first portion having a first height and a second portion proximal of the first portion and having a leading edge, the leading edge having a second height greater than the first height.

4. The staple driving assembly as recited in claim 3, wherein the difference between the first height and the second height is substantially equal to the distance required to drive the staple out of the staple containing pocket.

5. The staple driving assembly as recited in claim 3, wherein the elongated band includes a third portion intermediate the first portion and the second portion, the third portion tapering between the first and second portions such that movement of the elongated band beneath the staple containing pocket progressively drives the staple out of the staple containing pocket.

6. The staple driving assembly as recited in claim 3, wherein the elongated band has a constant height proximal of the leading edge.

7. The staple driving assembly as recited in claim 3, wherein the height of the elongated band decreases proximally of the leading edge.

8. The staple driving assembly as recited in claim 1, wherein the body portion includes:
the first staple containing pocket on a first side of the body portion;
the second staple containing pocket on a second side of the body portion; and
a post positioned intermediate the first and second sides of the body portion such that the elongated band passes from the first side around the post to the second side as the elongated band passes beneath the first and second staple containing pockets.

9. The staple driving assembly as recited in claim 8, wherein the post includes a roller movably mounted on the post such that the elongated band passes around the roller.

10. The staple driving assembly as recited in claim 8, wherein the body portion further includes a pusher positioned within the first staple containing pocket intermediate the staple contained within the first staple containing pocket and the elongated band.

11. A staple driving assembly comprising:
a cartridge having a body portion;
a first row of staples located in the body portion;
a second row of staples located in the body portion; and
an elongated band movably mounted within the body portion such that distal movement of the elongated band urges staples in the first row of staples out of the body portion and proximal movement of the elongated band urges staples in the second row of staples out of the body portion.

12. The staple driving assembly as recited in claim 11, wherein the elongated band is flexible.

13. The staple driving assembly as recited in claim 11, wherein the first row of staples is located on a first side of the body portion and the second row of staples is located on a second side of the body portion.

14. The staple driving assembly as recited in claim 13, further including a post positioned intermediate the first and second sides of the body portion such that the elongated bond passes from the first side of the body portion around the post to the second side of the body portion.

15. The staple driving assembly as recited in claim 14, wherein the post includes a roller movably mounted on the post such that the elongated band passes around the roller.

* * * * *